(12) United States Patent
DeMico et al.

(10) Patent No.: US 8,916,717 B2
(45) Date of Patent: Dec. 23, 2014

(54) DIOXASPIROKETAL DERIVATIVES, PROCESS FOR THEIR PREPARATION AND USES THEREOF

(75) Inventors: Antonella DeMico, Rome (IT); Andrea Cottarelli, Rome (IT); Mariapia Fuggetta, Rome (IT); Giulia Lanzilli, Rome (IT); Maria Tricarico, Rome (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 1586 days.

(21) Appl. No.: 12/227,228

(22) PCT Filed: May 10, 2007

(86) PCT No.: PCT/IT2007/000342
§ 371 (c)(1),
(2), (4) Date: Dec. 17, 2009

(87) PCT Pub. No.: WO2007/132496
PCT Pub. Date: Nov. 22, 2007

(65) Prior Publication Data
US 2010/0227919 A1    Sep. 9, 2010

(30) Foreign Application Priority Data

May 15, 2006    (IT) .............................. RM2006A0257

(51) Int. Cl.
C07D 493/10    (2006.01)
A61K 31/35    (2006.01)
C07D 407/04    (2006.01)

(52) U.S. Cl.
CPC ............ C07D 407/04 (2013.01); C07D 493/10 (2013.01)

USPC .......................................... 549/343; 514/460

(58) Field of Classification Search
None
See application file for complete search history.

(56) References Cited

FOREIGN PATENT DOCUMENTS

JP          10 007557 A    1/1998
WO        WO 00/00514 A2    1/2000

OTHER PUBLICATIONS

Perron et al., "Synthesis of Oxidized Spiroketals via 2-Furyl Ketone Oxidation-Rearrangement," J. Org. Chem., vol. 54, No. 9, 1989, pp. 2044-2047.*
International Search Report dated Sep. 27, 2007, International.

* cited by examiner

Primary Examiner — Sreeni Padmanabhan
Assistant Examiner — Jody Karol
(74) Attorney, Agent, or Firm — Hedman & Costigan, P.C.; James V. Costigan; Kathleen A. Costigan

(57) ABSTRACT

The invention relates to dioxaspiroketal derivatives of formula (I): wherein R, is selected from the group consisting of H, straight or branched chain $C_1$-$C_6$ alkyl, $C_1$-$C_6$ alkoxy, $C_2$-$C_6$ alkenyl, cycloalkyl, heterocyclyl, phenyl, optionally para-, meta- or ortho-substituted with 0 to 3 substituent selected from halogen, —CN, —$NH_2$, —OH, —$NO_2$, $COOR_2$, wherein $R_2$ is selected from H and $C_1$-$C_6$ alkyl, n is 1 or 2, X is O or S, $R_1$ is selected from H, OH, halogen, $C_1$-$C_6$ alkyl, $C_1$-$C_6$ alkoxy, $COOR_3$, wherein $R_3$ is selected from H and $C_1$-$C_6$ alkyl, or physiologically acceptable salts thereof, process for preparation thereof, their uses in medical field, in particular as anti-tumor medicaments.

1 Claim, 11 Drawing Sheets

DIOXASPIROKETAL DERIVATIVES, PROCESS FOR THEIR PREPARATION AND USES THEREOF

The present invention concerns dioxaspiroketal derivatives, process for their preparation, uses thereof in medical field, particularly as anti-tumour, anti-microbial and anti-fungal medicaments.

Dioxaspiroketal derivatives are present in several natural substances processed by a broad multiplicity of plants, bugs, microbes, fungi and sea organisms displaying interesting biological activities. They also belong to important macrolide spirane sub-units of polycyclic molecules with anti-fungal, anti-neoplastic and anti-helmintic, antibiotic, and insecticide activity, and they act as bioactive pheromones; in this group of substances there are spongistatins, avermectines, ionophor macrolides as calcimycin, bug pheromones and various marine origin derivatives among which BISTRAMMIDI and siphonarins (Smith et al, 2002; Perron, F. et al., 1989; Young et al., 2000; Gallagher et al., 2002).

The important bioactivity of this metabolites containing dioxaspirane subunits induced remarkable interest both from the synthetic and pharmacological point of view. From above, in addition to the fact that generally the extraction processes from natural sources are often very tedious and with limited yields, various synthetic strategies, also recently under development and refining, have been tried (Paterson et al., 2002).

Particularly, spongistatins are macrocyclic lactones containing six variously substituted pyrane rings, four of which are incorporated within two dioxaspirane subunits [5,5]. This group of cytotoxic macrolides is extracted in small amounts from different marine sponges.

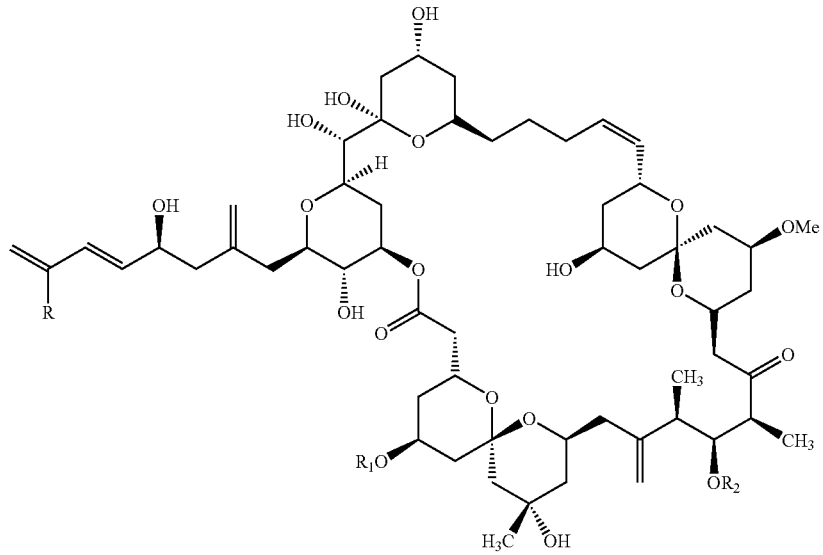

Spongistatin 1 R=Cl, $R_1$=$R_2$=COCH$_3$
Spongistatin 2 R=H, $R_1$=$R_2$=COCH$_3$
Spongistatin 3 R=Cl, $R_1$=H, $R_2$=COCH$_3$
Spongistatin 4 R=Cl, $R_1$=COCH$_3$, $R_2$=H
Spongistatin 6 R=H, $R_1$=COCH$_3$, $R_2$=H

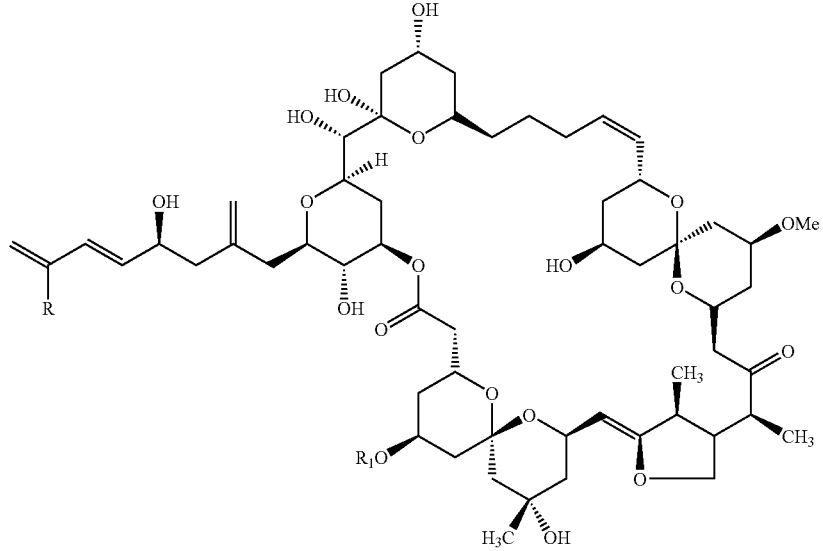

Spongistatin 5 R=Cl, R₁=H

Spongistatin 7 R=H, R₁=H

Spongistatin 8 R=H, R₁=COCH₃

Spongistatin 9 R=Cl, R₁=COCH₃

Recently Uckun (Uckun et al., 2000) and its co-workers extracted spongistatin 1 from marine sponges of *Hytrios* genus occurring in Indian Ocean. The latter displayed elevated cytotoxicity with IC$_{50}$ sub-nanomolar values against 60, both haematological and epithelial human cancer cell lines belonging to a NCI panel (National Cancer Institute).

The high anti-neoplastic activity of the spongistatins is correlated to their capacity in inhibiting the microtubules assembling and therefore the tubulin polymerization, in addition to the interactions of tubulin itself with vinca nucleotides and the alkaloids, which would occur in absence of such natural substance.

The microtubules, consisting of 2 globular polypeptides, i.e. α and β tubulins, play a key role in the formation of the mitotic spindle. By means of a 3D atomic model of tubulin αβ dimer, it has been possible to identify the putative binding site of spongistatins with the tubulin. The bond of spongistatin with this site therefore can affect the interaction between the tubulin dimers resulting therefore in the de-polymerization thereof. The anomalous tubulin polymerization prevents the formation of the microtubule and mitotic division is stopped.

BISTRAMMIDI are naturally occurring substances extracted from marine sources, among which tunicates from *Didemnidae Ascidiacea* species (Biard et al., 1994). Particularly from *Lissoclinu bistratum* colony five similar compounds, named BISTRAMMIDI, A, B, C, D and K have been isolated. BISTRAMMIDI B, C and D differ from A due to the oxidation states in the region of C2-C4 and C36-C39 terminal bonds. The A-D structures consist of a tetrahydropiran ring and a dioxaspiroacetal unit, bonded together with γ-amino acid peptide chain (Gallagher et al., 2002).

Bistratene A

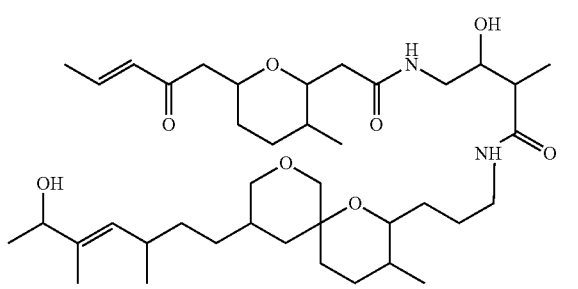

Bistrammide B

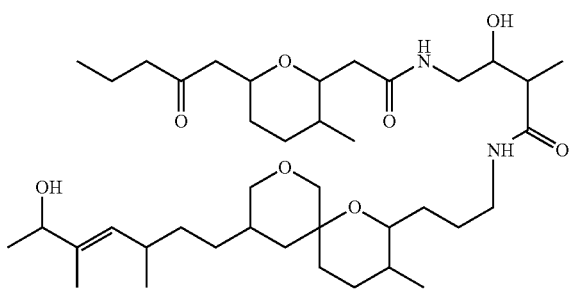

Bistrammide C

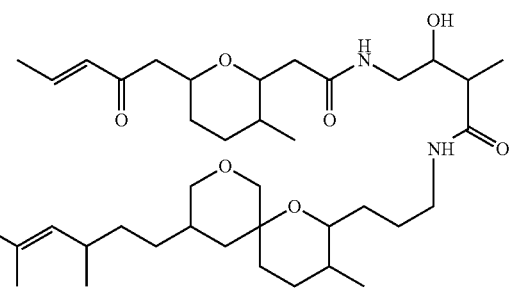

Bistrammide D

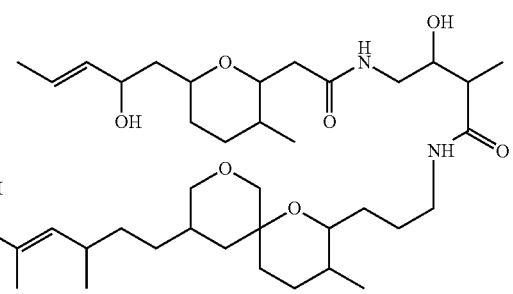

Bistrammide K

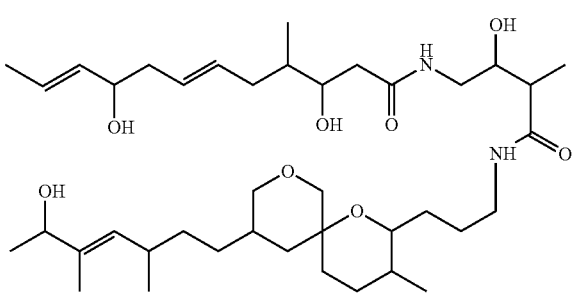

BISTRAMMIDE A, also named Bistratene A, displays high anti-tumour activity in vitro, penetrates the cellular wall and is the unique substance reported as a specific activator of Cδ protein kinase, a PKCs isoform (Watters et al., 1998).

All PKCs are involved in the signal translation for the cell proliferation, differentiation and apoptosis, processes having remarkable importance in anti-cancer therapy. The activity of this substance has been tested on cell lines of human melanoma (MM96E) and, by means of biological assays, its capacity to induce both morphologic and functional differentiations on such cells has been confirmed.

The interest in synthetic chemistry is particularly focused on the synthesis of dioxaspiroketal fragments whose basic ring is among the following ones; these, in fact, are found with greater frequency in most of the natural substances (Perron. et al., 1989).

a)

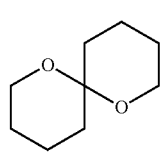

b)

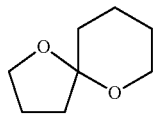

c)

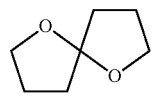

a) 1,7-dioxaspiro[5.5]undecane
b) 1.6-dioxspiro[4,5]decane
c) 1,6-dioxaspiro[4,4]nonane.

Papers about the synthesis of the dioxaspiranes are various and comprise the most different methodologies (Perron et al., 1989). In order to show a concise and clear picture comprising almost all synthetic routes, we believe to be useful to include the same in three very broad and general classes, based on the formation of the bond for the production of the precursor to be cyclized.

Generally the most frequently employed synthetic strategy is one using as an attachment point a carbonyl group, that will subsequently become the spirane carbon atom.

The three classes are following:
1) formation of the $C\alpha$-$C_{spiro}$ bond
2) formation of the $C\alpha$-$C\beta$ bond
3) oxidative rearrangement of furan and derivatives thereof.

It is worthy to point out that, although various synthetic strategies for the spiroketal synthesis have been developed, the acid-catalysed cyclization of dihydroxyketone or similar molecules still is the most important and most widely used process The individual methodologies are detailed in the following.

1) Formation of $C\alpha$-$C_{spiro}$ Bond

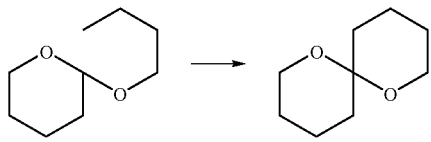

This synthetic strategy can be used in order to obtain both symmetric and asymmetric compounds, depending on the used precursors.

In this class various very different synthetic approaches are included: the basic differentiation is based on the precursors used to obtain spiroketal; one of these approaches uses 1,3-dithianes or equivalent acyl anions as reagents to bind two hydroxyl alkyl groups to a pro-carbonyl group that will become the spirane carbon atom. As an example the synthesis according to Thomas (Smith et al., 2002) involving the step of alkylation-dithian epoxide ring opening followed by hydroxyl alcohol groups de-protection and spiro-cyclization in acid environment is reported.

Another approach involves the alkylation of vinyl ethers: generally an already formed ring is used to which second ring members are added, and then the latter will be obtained by means of acid-catalysed spiro-cyclization. An example the synthesis according to Amouroux (Amouroux R., et al., 1984) is reported, wherein dihydropyran is de-protonated using BuLi and then alkylated using a protected alcohol iodide. Alcohol deprotection allows the second ring formation, resulting in the generation of [4.5], or [5.5] spiro system, according to the alkyl chain length of the starting alcohol.

Another most representative synthesis to produce bistratene spiroketal fragment is as reported by Gallagher and co-workers (Gallagher et al., 2002): the precursor is open chain ketoalcohol which is alkylated using dioxolane iodide. The resulting product is spiro-cyclized in acid environment.

From above described reactions it is apparent that, although numerous, many involve a great number of steps and often yields thereof are not elevated; moreover, as it is clear in Thomas synthesis, in order to obtain variously functionalised dioxaspiranes it is not always possible to modify a basic strategy, but it is often necessary to re-formulate the same using new starting materials and different reaction conditions. It is apparent that this involves numerous disadvantages for the production resulting in longer reaction times and increased cost.

2) Formation of $C\alpha$-$C\beta$ Bond

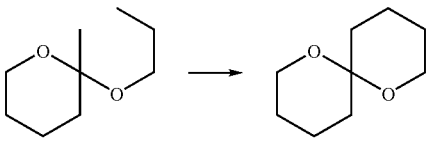

Many of the strategies in this class involve the use of enolate or similar anions, wherein carboxyl group will be in the final product the spirane carbon atom.

An example is the synthesis according to Still and Kishi (Perron et al., 1989), based on the joining of two large fragments by means of aldol type condensation, in order to obtain a precursor which is then cyclised. As it is shown in the following reaction scheme, it is necessary to modify the cyclization reactions conditions depending on the different functional groups on the chains.

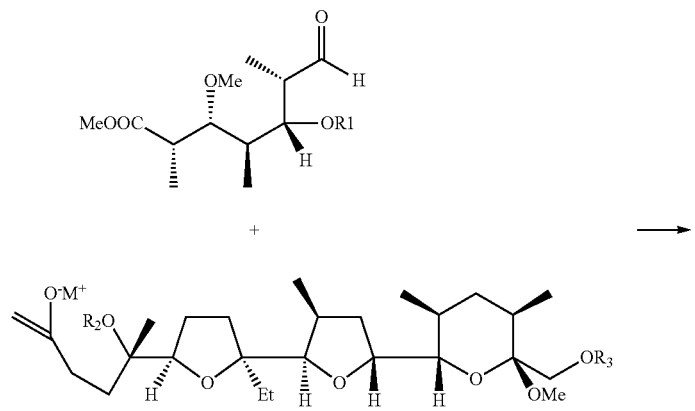

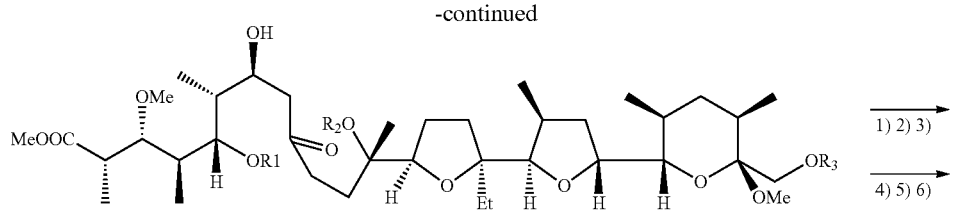

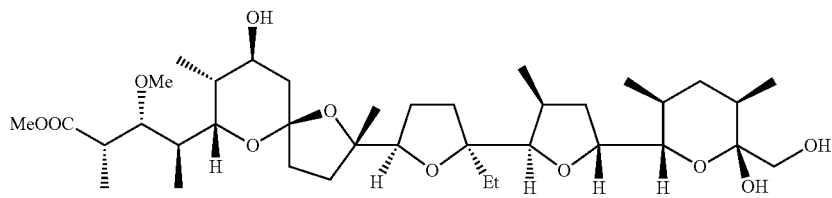

When

R$_1$=SiEt$_3$ 1) H$_2$/Pd/C Et$_2$O

R$_2$=SiEt$_3$ 2) pTsOH/CH$_2$Cl$_2$/Et$_2$O/H$_2$O

R$_3$=Bz 3) NaOH/MeOH$_{aq}$

When

R$_1$=Bz 1) H$_2$/Pd/C CH$_3$OH/HOAc

R$_2$=H 2) CSA/CH$_2$Cl$_2$/Et$_2$O (3:1) room temperature, 30 minutes

R$_3$=H 3) NaOH 1N/CH$_3$OH

One of the syntheses according to a quite general route is according to Paterson (Amouroux R., 1984), provided to obtain spongistatin 1 spiroacetal C-D subunit. This synthesis involves a tedious construction of the carbon backbone, essentially by means of aldol condensation reactions; thus obtained linear fragment by treatment with aqueous HF in acetonitrile is cyclised resulting in spiroacetal sub-unit.

In conclusion, C-D sub-unit is obtained through several synthetic steps and using not easily commercially available reagents thus resulting in high final costs.

3) Oxidative Rearrangement of Furan and Derivatives Thereof.

This type of synthesis, differently than above described, involves the use of more easily available reagents, like furan derivatives, and molecules containing few carbon atoms Oxidative rearrangement of 2-furyl carbinols to dihydropiranones can be carried out starting from several reagents, like molecular bromine, per-acids, PCC.

This approach, using an oxidation for the synthesis of dioxaspiroketals, has been used by De-Shong (Smith et al., 2002). According to it appropriately functionalized 2-furyl-carbinols are obtained from furan by α-metalation followed by alkylation; the subsequent oxidative transposition with m-CPBA results in emi-acetal that by treatment with HF in acetonitrile, is de-protected and spiro-cyclised.

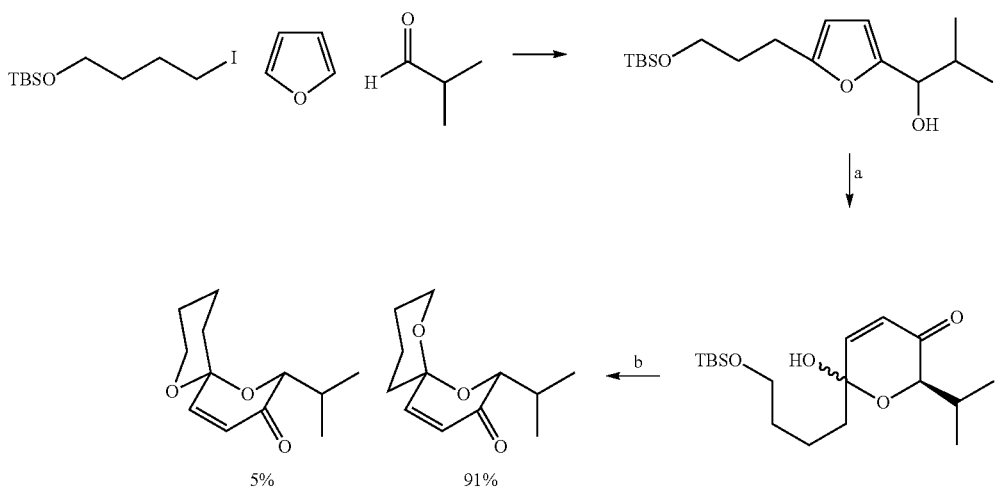

a) m-CPBA, CH$_2$Cl$_2$, 90%; b) HF/CH$_3$CN

In order to obtain variously functionalised and with higher number of oxygen atoms dioxaspiranes, the strategy according to De-Shong has been modified by Perron (Perron et al., 1989), who uses previously alkylated furans for subsequent lactone alkylation.

In these reaction conditions the resulting precursor can only exist in open chain form. The treatment of the latter with NBS in aqueous THF results in the chain closure and furan rearrangement in order to obtain dioxaspirane.

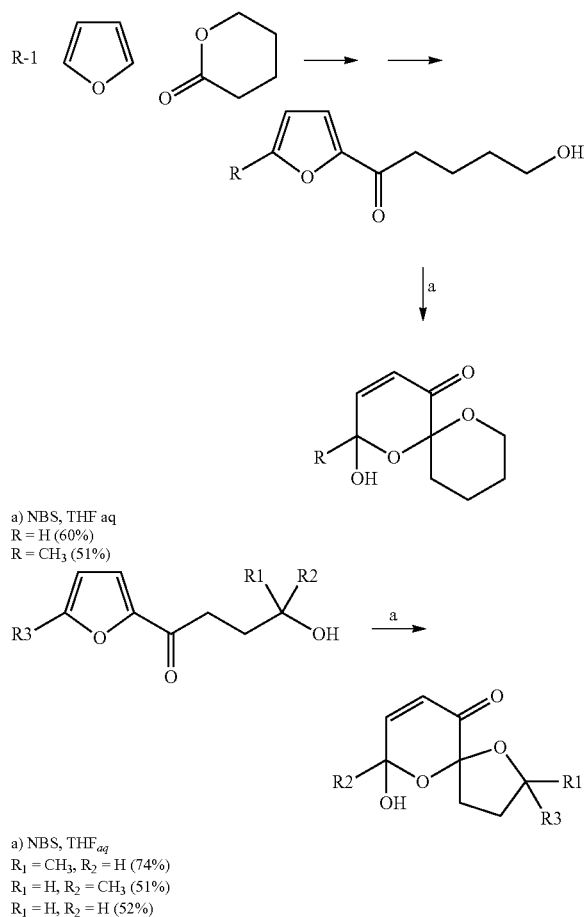

a) NBS, THF aq
R = H (60%)
R = CH$_3$ (51%)

a) NBS, THF$_{aq}$
R$_1$ = CH$_3$, R$_2$ = H (74%)
R$_1$ = H, R$_2$ = CH$_3$ (51%)
R$_1$ = H, R$_2$ = H (52%)

Although this last approach is, among those up to now described, the unique that allows the formation of the dioxaspiran system through simple reactions, few steps and in high yields using easily commercially available and cheap reagents, yet displays disadvantages. The first and most apparent is that using alkyl substituted furan derivatives yields are lowered. Further during the reaction the lactone ring is opened and this does not allow the ring functionalization necessary for the introduction of substituents present in pharmacologically active macrolides. This strategy proves to be not suitable when in a position at the reaction centre an oxygen atom is present, because no usual oxidant is suitable to transform furan into pyrane nucleus.

Almost all currently available chemotherapeutics kill cancer cells by blocking DNA synthesis, i.e. interfering on mitosis or blocking other functions of the cell cycle or inducing cell apoptosis.

The cell cycle starts with G1 step, believed to be the growth step wherein the cell regenerates the enzymatic kit and repairs the damages. Step S (Synthesis) follows wherein DNA is doubled by DNA polymerase enzyme. G2 step, wherein the cell produces the organelles indispensable for the division (centrioles), follows. In the step M (mitosis), the last one, cell division occurs.

Apoptosis is a cell typical phenomenon of pluri-cellular organisms and essentially consist of a "scheduled cell death", whose function is to contribute, together with mitosis, to the maintenance of numerical homeostasis Apoptosis death involves a complex network of intercellular signals. Volume of apoptotic cell quickly diminishes by condensation, the cell rapidly detaches from the next ones and the nucleus is fragmented. The resulting fragments reach later the plasmatic membrane wherein they are enclosed in evaginations of the same membrane conferring a bubble cell appearance.

Telomeres represent the end of eukaryote linear chromosomes and they are essential elements for chromosome stability, their duty being to protect the same during cell division. Telomerase is RNA-dependent polymerase with reverse transcriptase activity; it adds repetitive hexamer sequences (TTAGGG) to chromosome ends in dividing cells. By means of such mechanism, telomerase provides chromosome stability and prevents cellular aging. The regulation of the telomerase activity in the cells plays a very important role in the carcinogenesis. In the tumour but not in differentiated cells or healthy tissues high telomerase activity is detected. In the healthy cells, in the absence of telomerase activity, the telomeric sequences during the cell division are progressively shortened, until the cell does not proliferate any more. Most tumour cells with indefinite proliferation capacity, maintain the telomeres by expressing telomerase activity always associated with the expression of the reverse transcriptase catalytic sub-unit of human telomerase (hTERT).

From above it is apparent the need of providing a new process for the synthesis of dioxaspirane sub-units, also variously functonalized on both rings, analogous to those occurring on above said macrolides, allowing to circumvent the drawbacks of previously described synthetic routes. It is also felt the need for the availability of new active principles to be used advantageously as anti-tumour, antibiotic medicaments, as an alternative to currently available anti-tumour compounds, suitable to act at the telomerase level, in order to overcome the drug-resistance and toxicity problems against healthy cells.

The authors of the present invention have found now a process for the preparation of dioxaspirane sub-units by means of oxidative transposition starting from furan and lactone derivatives, which, otherwise than the synthetic methodologies of known art, allows the skeleton of dioxaspirane fragment, starting from easily available reagents (furylcarbinols and lactone derivatives), to be obtained, through few and simple reaction steps and in high yields. Further it is possible to functionalise both rings of dioxaspirane derivatives in such way to allow subsequent transformations to be carried out in order to introduce necessary substituents so that such systems are as similar as possible to those present in the natural macrolides. The products are obtained as diastereomeric mixtures and it has been possible to assess the predominance of a particular structure, as evidenced by means of spectroscopic analysis (see Example 1).

Using this process it is possible to promote simultaneously rearrangement and spiroketalization of furylcarbinols with oxygen in α-position. In fact, the provided oxidation conditions allow alcohols having an oxygen atom in α-position to be used as substrates because currently there are no classical oxidants suitable for direct oxidative rearrangement. Various oxidants useful to be used for promoting furan ring rearrangement to pyrane system in furylcarbinols are available, like m-CPBA, iodobenzene diacetate (BAIB), pyridinium chlorochromate (PCC) and various peroxides (March, 1992). Everyone of these displays limiting oxidation activity when tertiary furyl alcohol has α-oxygen substituent while, when the heteroatom is present on the ring in other positions, the reaction proceeds with high yields. Therefore the direct synthesis of dioxapiranes starting from furan derivatives is not currently possible, being possible only through several steps.

The characteristic differentiating our synthesis route from those known in the art is the possibility to obtain variously functionalised dioxapyranes merely by means of not important modifications on starting reagents, without the need to re-adapt the reaction conditions based on the designed final product. The possibility that variously functionalised intermediates to be synthesised further allows biochemical screening assays to be carried out in order to evaluate various ring substituent effect on the bioactivity of these compounds.

A further aspect of the invention concerns dioxaspiroketal derivatives representing a new class of synthetic compounds to be advantageously used as anti-tumour, anti-microbial and anti-fungal medicaments.

Therefore it is an object of the present invention dioxaspiroketal derivatives having the formula (I):

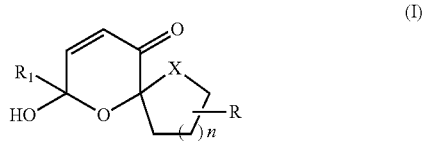

(I)

wherein R, can be selected from the group consisting of H, straight or branched chain $C_1$-$C_6$ alkyl, $C_1$-$C_6$ alkoxy, $C_2$-$C_6$ alkenyl, cycloalkyl, heterocyclyl, phenyl, optionally para-, meta- or ortho-substituted with 0 to 3 substituent selected from the group consisting of halogen, —CN, —NH2, —OH, —NO$_2$, COOR$_2$, wherein R$_2$ is selected from H and $C_1$-$C_6$ alkyl,
n can be 1 or 2,
X is heteroatom selected preferably from O and S,
R$_1$ can be selected from H, OH, halogen, $C_1$-$C_6$ alkyl, $C_1$-$C_6$ alkoxy, COOR$_3$, wherein R$_3$ can be selected from H and $C_1$-$C_6$ alkyl,
or physiologically acceptable salts thereof.

Heterocycle in the context of the present invention means pyrrole, furan, thiazole, pyridine, indole, benzofuran.

In a preferred embodiment of the invention n is 2, X is O, R is H, and R$_1$ is H.

According to another embodiment of the present invention, n is 2, X is O, R is H and R$_1$ is CH$_3$.

In a preferred embodiment of compounds according to the invention, n is 1, X is S, R is H and R$_1$ is H.

According to a further embodiment of inventive derivatives, n is 1, X is O, R is phenyl and R$_1$ is H.

The present invention concerns further derivatives wherein preferably n is 1, X is O, R is CH$_3$ and R$_1$ is H.

In a further preferred embodiment of the inventive derivatives, n is 2, X is O, R is pentyl and R$_1$ is H.

The derivatives according to the invention are preferably compounds wherein n is 2, X is O, R is CH$_3$ and R$_1$ is H.

Alternatively in a preferred embodiment of the present inventive derivatives n is 2, X is O, R is CH$_3$ and R$_1$ is CH$_3$.

In the preferred embodiments of the inventive derivatives, when R is other than H it is preferable R to be in position 2 of the ring.

In a further embodiment of the invention, when R is CH$_3$ and it is in 2 position of the ring, dioxaspiroketal derivatives having formula (I), can have a further methyl group in 4 position of the ring.

Alternatively in a preferred embodiment of the present invention the derivatives of the present invention said ring can have double unsaturation.

In a further embodiment of the inventive derivatives in the above reported embodiments the double bond is optionally replaced with halogen or OH group.

Preferably, said dioxaspiroketal derivatives are selected from the group consisting of 1,7 dioxa spiro[5,5]undec-5-oxa-3-en-2-ol, 1,7 dioxa spiro[5,5]-10-methyl-5-oxa-undec-3-en-2-ol, 1,7 dioxa spiro[5,5]undec-5-oxa-3-en-2-methyl-2-ol, 1,6 dioxa spiro[4,5]-3-methyl-10-oxa-dec-8-en-7-ol, 1,7 dioxa spiro[5,5]-10-pentyl-5-oxa-undec-3-en-2-ol, 1,6 dioxa spiro[4,5]-3-phenyl-10-oxa-dec-8-en-7-ol, oxa-6-thio spiro[4,5]-10-oxa-dec-8-en-7-ol.

Derivatives according to formula (I) represent a further object of the present invention for use in medical field.

A further object of the present invention is the use of compounds according to formula (I) for the preparation of a medicament for the treatment of the solid or liquid tumours. Preferably said solid tumours are carcinomas, selected from the group consisting of ovary, thyroid, colon, pancreas, breast, gastric, prostate, lung carcinoma. Said liquid tumours I are leukemias.

Further the invention concerns the use of compounds of formula (I) for the preparation of antibacterial or antifungal medicament.

Another object of the present invention is pharmaceutical composition comprising at least one of above described compounds according to formula (I), as active principles, together with one or more pharmacologically acceptable adjuvants and/or excipients.

A further object of the present invention is a process for the preparation of dioxaspiran and/or dioxaspiroketal derivatives thereof; comprising the following steps:

a) formation of the furan derivative through the bonding of a carbonyl compound to furan nucleus by means of lithiation with a lithiating agent, preferably BuLi, in the presence of inert atmosphere, anhydrous solvent, basic catalyst, preferably TMEDA, to obtain a tertiary alcohol;

b) rearrangement of the product obtained in step a) by means of oxidation with NBS in THF/H$_2$O. Preferably, said THF/H$_2$O mixture is at 4:1 ratio.

NBS is a widely employed oxidant for brominating reactions, both for radical substitutions and electrophilic additions. In fact it is suitable to generate bromine in situ, which is hardly usable such it is because of remarkable solution instability (Watters et al., 1999).

The role of the NBS in step b) is fundamental because it acts as nucleophilic agent and therefore indispensable in order to introduce the hydroxyl group. The NBS oxidative property allowing to promote the simultaneous rearrangement and spiroketalization of furylcarbinols having α-oxygen are affected from the number and the type of substituents in side chain in the reaction centre and functional groups on forming cycles. When the substituent is a C$_5$ or more hydrocarbon chain the spiroketalization process does not occur possibly due to steric effects but anyway the product can be obtained in good yields by addition of catalytic amount of an acid catalyst as camphorsulfonic acid (Baker, 1989). NBS allows the direct synthesis of dioxaspiranes starting from furan derivatives by means of a transposition mechanism with a radical in addition to cationic component.

The solvent used in step b) is preferably THF (very pure) and $H_2O$, pH 7, preferably buffered, mixture at 4:1 ratio; the reaction must be carried out at low temperature (preferably below 5° C.) by NBS addition to reaction mixture in solid portions (2:1 ratio) very slowly and only when yellow-orange colour, indicating bromine in excess, has disappeared. Exceeding NBS then must be destroyed before the organic solvent evaporation.

According to a preferred embodiment the step a) is carried out by addition to furan of BuLi (1-2 M) and TMEDA at 1:1 ratio with respect to furan in anhydrous ether and stirring the mixture for 3 hours. TMEDA presence is necessary for n-BuLi de-polymerization from the hexameric to the monomeric form, through the coordination of Li atom to bidentate ligand nitrogen.

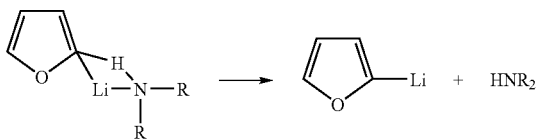

Then the lactone in anhydrous ether solution is added thereto at 0° C. The reaction progress can be monitored by means of thin layer chromatography (TLC) plates eluting with Etpet/AcOEt at various ratios using UV lamp and $H_2SO_4$ 5N for detection. The mixture is treated with $NH_4Cl$ aqueous saturated solution and extracted with diethyl ether. Products are identified using $^1H$ NMR analysis.

According to a particular embodiment of the present invention step b) can additionally comprises the addition of another acid catalyst, preferably camphorsulfonic acid (CSA). CSA is preferably added as $CH_2Cl_2$ solution.

The progress of the reactions can be monitored by means of thin layer chromatography TLC) eluting with Epet/AcOEt at different ratios and spots detected by means of UV lamp and $H_2SO_4$ 5N. The reaction mixture has been then washed with $Na_2S_2O_3$ and $Na_2HCO_3$ saturated solution, subsequently extracted with $CH_2Cl_2$, washed again with NaCl saturated solution and finally again extracted with $CH_2Cl_2$. Finally the products are identified using $^1H$ NMR analysis.

In a preferred embodiment of the preparation process according to the invention in step a) said lithiating agent is BuLi 1.6 M, said solvent is anhydrous diethyl ether and said inert atmosphere is generated using nitrogen.

According to a preferred embodiment of the step a) in the preparation process according to the present invention the furan nucleus is selected from furan and $C_{1-6}$ alkyl group substituted furan and the carbonyl compound selected from δ-valerolactone and $C_{1-6}$ alkyl group substituted δ-valerolactone.

Finally, the compounds of general formula (II) represent a further object of the present invention):

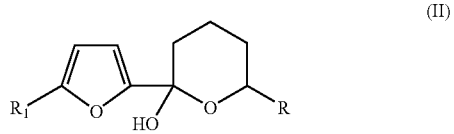

(II)

wherein R and $R_1$ are defined as above.

It is necessary yet to point out that NBS oxidation properties are highly dependent on the substituent type in side chain at the reaction centre and functional moieties on the forming cycles.

In the preparation of third compounds it has been necessary to add catalytic amounts of another catalyst, preferably camphorsulfonic acid (CSA), as adjuvant for the spiroketalization, because it has been assumed that the failing in the second ring formation was due to substituent steric hindrance. Preferably, these catalytic amounts of catalyst are added in portions until a maximum of 40-45% with respect to NBS.

The present invention now will be described by illustrative, but not limitative way, according to preferred embodiments, with particular reference to the enclosed drawings wherein.

Figure 11A:
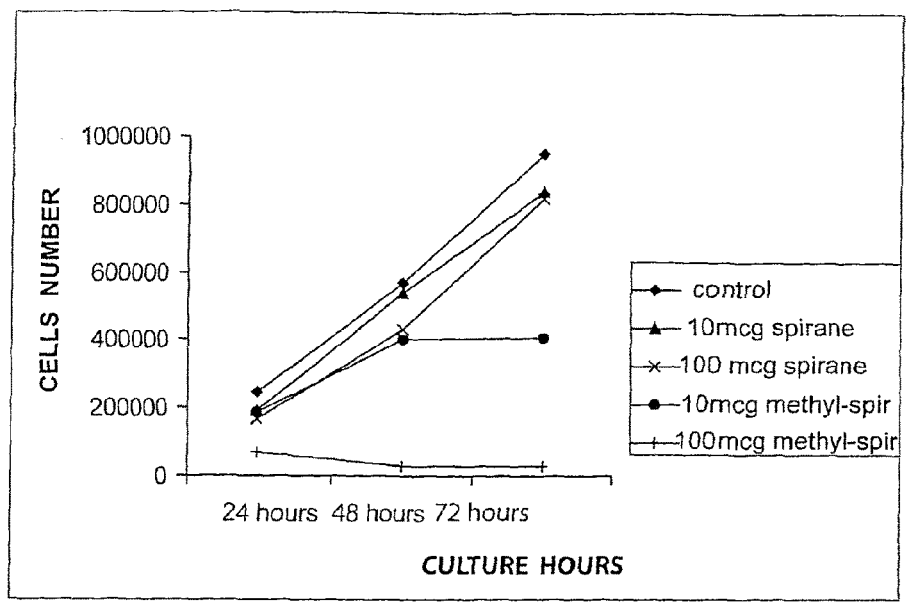
Figure 11B:
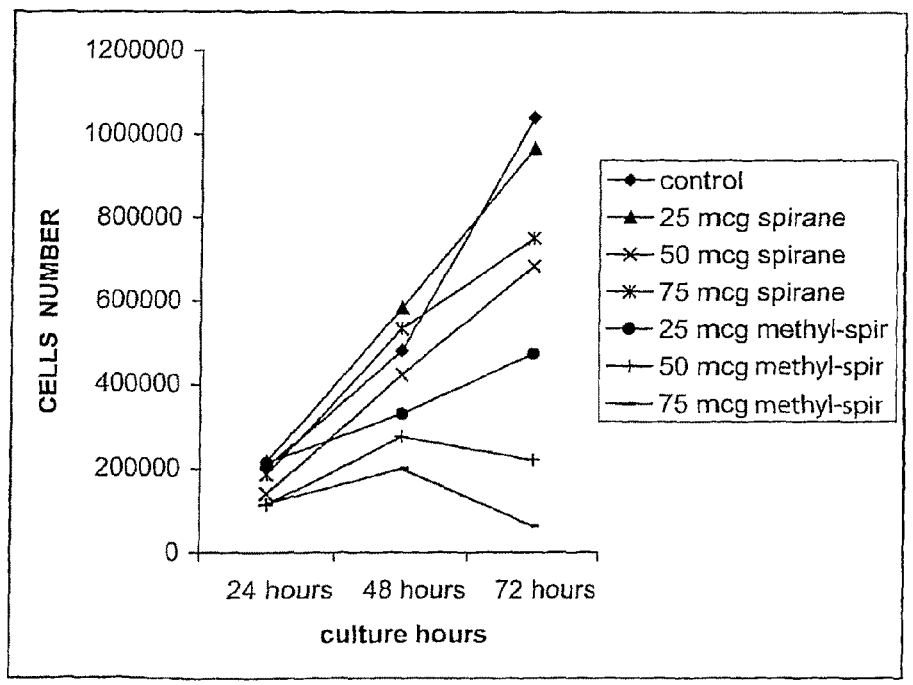

FIG. 11, panels A-B, shows the comparison of spirane and methyl spirane effect at various concentrations (panel A: 10, 100 mcg; panel B: 25, 50, 75 mcg) on the growth of M14 melanoma cells.

EXAMPLE 1

Processes for the Preparation of Dioxaspiroketal Derivatives

Materials and Methods:

$^1$H NMR spectra have been registered using a Varian Gemini 200 MHz spectrometer. Merck 60 silica gel and Merck 60 $F_{245}$ silica gel 0.25 mm thick plates were used for column and thin layer (TLC) chromatography, respectively. Carl Erba RPE grade solvents were used.

Synthesis of 1-furyl tetrahydropyranol

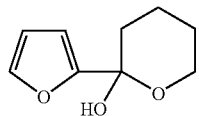 [SMILES: OC1(c2ccco2)CCCCO1]

Preparation 0.98 ml BuLi (1.6 M) are added at 0° C. to mixture of 1.28 ml (ρ=0.936) furan (1.5 mmol) and 0.22 ml (ρ=0.774) TMEDA (1.51 mmol) in 10 ml anhydrous diethyl ether under stirring in inert atmosphere, at room temperature. After 3 hours the reaction mixture is cooled at −78° C. and 0.20 ml (ρ=1.079) δ-valerolactone (2.10 mmol) in approximately 2 ml anhydrous diethyl ether are added. After approximately 1 hour the mixture is washed with NH$_4$Cl saturated solution, the aqueous layer is extracted three times with Et$_2$O and the ether extracts are dried on anhydrous Na$_2$SO$_4$ and cold evaporated under reduced pressure. The product is isolated by silica gel chromatography eluting with petroleum ether/ethyl acetate 2:1. The yield is 87%.

$^1$H-NMR Data:

δ=1.6 (m, 2H); δ 1.8 (m, 2H); δ=2.35 (s, 1h); δ=2.9 (t, 2H); δ=3.7 (t, 2H); δ=6.55 (dd, 1H); δ=7.25 (d, 1H); δ=7.6 (d, 1H).

Synthesis of 1-furyil-5-methyl-tetrahydropyranol

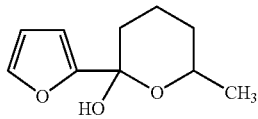

Preparation:

BuLi (1.6 m) is added at 0° C. to a mixture of furan and TMEDA in anhydrous diethyl ether under stirring in inert atmosphere at room temperature. After 3 hours the reaction mixture is cooled at −78° C. and δ-esanolactone in anhydrous diethyl ether is added. After approximately 1 hour the mixture is washed with NH$_4$Cl saturated solution, the aqueous layer is extracted three times with Et$_2$O and the ether extracts are dried on anhydrous Na$_2$SO$_4$ and cold evaporated under reduced pressure. The product is isolated by silica gel chromatography eluting with petroleum ether/ethyl acetate 2:1. The yield is 89%.

$^1$H-NMR Data

δ=1.3-1.4 (d, 3H); δ=1.5 (m, 2H); δ 1.85 (m, 2H); δ=2.8 (t, 2H); δ=3.8 (q, 1H); δ=6.55 (dd, 1H); δ=7.2 (d, 1H); δ=7.6 (d, 1H).

Synthesis of 1-[(5-methyl)-2-furyl]-tetrahydropyranol

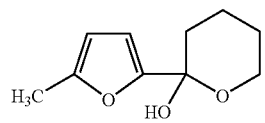

Preparation:

9.50 ml BuLi (1.6M) are added at 0° C. to a mixture of 1.28 ml (ρ=0.916) methylfuran (14.3 mmol) and 2.18 ml (ρ=0.774) TMEDA (14.5 mmol) in 40 ml anhydrous diethyl ether under stirring in inert atmosphere, at room temperature. After 3 hours the reaction mixture is cooled at −78° C. and 1.86 ml (ρ=1.079) δ-valerolactone (20 mmol) in approximately 2 ml anhydrous diethyl ether are added. After approximately 1 hour the mixture is washed with NH$_4$Cl saturated solution, the aqueous layer is extracted three times with Et$_2$O and the ether extracts are dried on anhydrous Na$_2$SO$_4$ and cold evaporated under reduced pressure. The product is isolated by silica gel chromatography eluting with petroleum ether/ethyl acetate 2:1. The yield is 61%.

$^1$H-NMR Data:

δ=1.65 (m, 2H); δ 1.8 (m, 2H); δ=2.1 (s, 1H); δ=2.85 (t, 2H); δ=3.7 (t, 2H); δ=6.2 (dd, 1H); δ=7.5 (d, 1H).

Synthesis of Dioxaspiroketal Derivatives a) 1,7-dioxaspiro[5,5]-undecen-3-en-5-oxa-2-ol

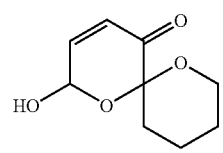 [SMILES: O=C1C=CC(O)OC12CCCCO2]

b) 1,7-dioxaspiro[5,5]-8-methyl-5-oxa-undec-3-en-2-ol

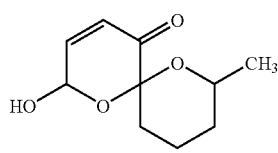

c) 1,7-dioxaspiro[5,5]-undecen-3-en-5-oxa-2-ol-2-methyl

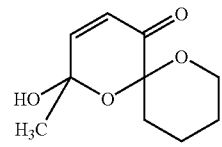

General Procedure:
A suitably calculated amount of NBS at 0° C. is added at 2:1 ratio to furylcarbinol in THF/H$_2$O (pH=7) 4:1 under stirring and the reaction mixture is stirred for approximately 1 hour and 30 minutes.

The following scheme depicts the synthesis process according to the invention:
Step a)

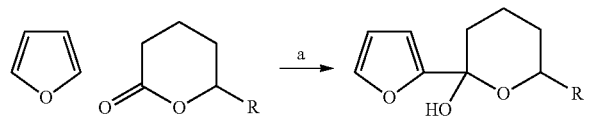

BuLi (1.6 M), anhydrous Et$_2$O, N$_2$, TMEDA
Step b)

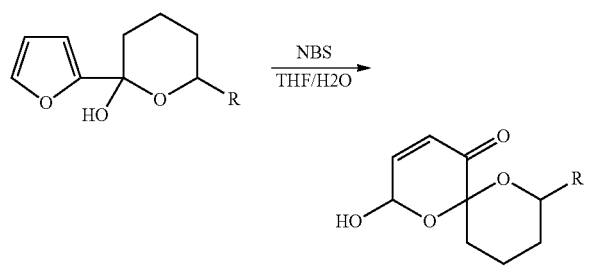

Particularly, for above reported compounds. i.e. a), b) and c), the reaction steps have been carried out according to the following scheme:

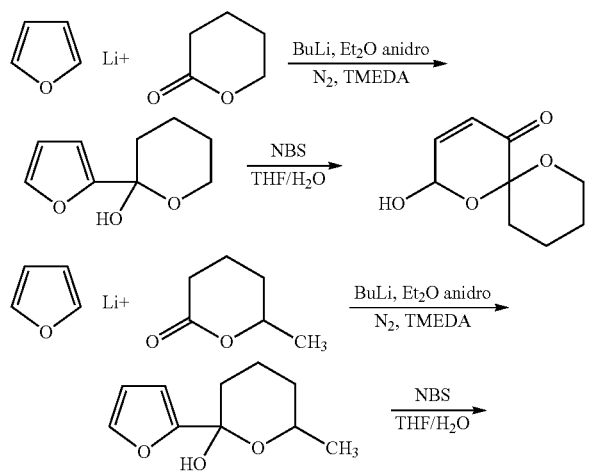

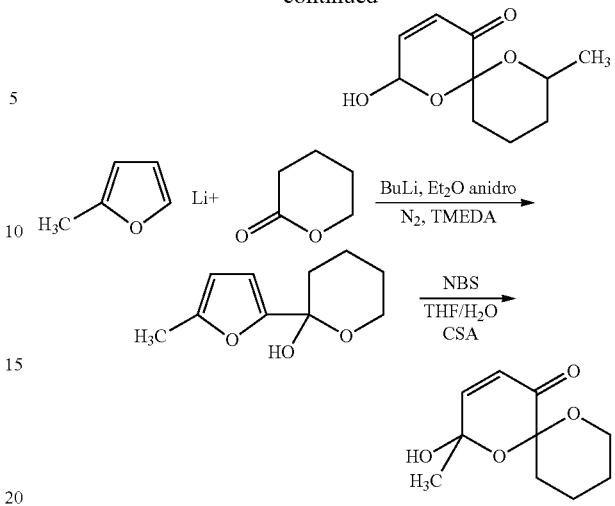

After TLC control and neutralisation reaction mixtures are extracted three times with CH$_2$Cl$_2$. The organic layer is washed with NaCl saturated solution and finally again extracted with CH$_2$Cl$_2$; the resulting residues are dried on anhydrous Na$_2$SO$_4$ and cold evaporated at reduced pressure. The product is isolated by silica gel chromatography eluting with petroleum ether/ethyl acetate at different ratios depending on the substrate.

Theoretical yield calculated by gas-chromatography is 92-98% depending on the product. The chromatographic yields of the products, however, are variable from 58 to 70%. This is principally due to the fact that furylcarbinols are very reactive and unstable compounds and the formation of the product is affected from furylcarbinol oxidation potential, and steric hindrance limiting the furan ring opening and subsequent rearrangement to pyrane system.

Also in this case the yields are substantially dependent on the accuracy of the reaction conditions and operation carrying out.

Dioxaspirane structures have been identified by means of $^1$H NMR and characteristic data have been previously reported.

Chemical-Physical Properties

Spiroketals are oily, photosensitive, thermounstable, variably coloured, namely from intense yellow to the dark orange, compounds, whereby their processing must be carried out at low temperature. 1,7-dioxaspiro[5,5]undecane compound is easily identifiable by $^1$H-NMR and $^{13}$C-NMR, the molecule is symmetrical and displays only half of signals due to overlapping thereof. $^1$H-NMR spectra (CDCl$_3$) are characterised by four signals having the following chemical shifts (ppm): 1.30 (m, 8), 1.64 (m, 2), 1.93 (m, 2), 3.60 (m, 4); $^{13}$C-NMR spectra present five signals: 19.1, 25.8, 36.2, 60.2, 94.9. Other characteristic data are: MW=156.23; bp=193° C.; n$_d^{20}$=1.4640; ρ=1.020; fp=147° F.

Spectroscopic Analysis:
The characterisation of the furyilcarbinols has been carried out by $^1$H NMR analysis; recorded spectra are reported in the following. Typical chemical shift values of basic furyilcarbinol are 6.55, 7.25, 7.55 ppm for protons on the furan ring; 3.7 ppm for methylene in oxygen atom α-position of lactone ring. If methyl group occurs on furan ring a 2.2 ppm signal will be present; when the latter is on lactone ring a 1.38 ppm signal will be present.

In some cases It has been possible to detect the presence of the diastereoisomers, as it is apparent from the spectrum wherein a 1.4 ppm signal relative to diastereoisomeric methyl is present.

The characterisation of the dioxaspirani has been carried out again by $^1$H NMR analysis. Typical chemical shift values of basic dioxaspirane, i.e. 1,7-dioxaspiro[5,5]-undecen-3-en-5-oxa-2-ol, are: 6.95 and 6.15 ppm relative to olefinic protons, 5.57 ppm for proton in alcoholic group α-position, and finally 3.82 ppm for methylenic protons. If a methyl group is present in oxygen α-position on the ring resulting from the lactone, a 1.82 ppm signal will be observed when the methyl group is on the ring resulting from the furan a 1.52 ppm signal will be present. As before it has been possible to detect the presence of diastereoisomers.

The oxidation products, in fact, are susceptible to transformations: i.e. epimerization and ketal nucleus opening. These phenomena are generally observed when the product is stored in weakly acid solvents or in the presence of substituents promoting the ring opening. Based on spectroscopic data it is possible to assume that the main reaction product is one wherein the dioxaspirane rings are orthogonal each to other.

EXAMPLE 2

Study on the Anti-Tumour Biological Activity of Dioxaspiroketal Compounds

The biological activity of spiranes has been studied in various human and murine tumour cell lines, evaluating the effects of these compounds on cell growth, death, apoptosis induction, cellular cycle and telomerase.

After the synthesis, methyl-spirane (1,7-dioxaspiro[5,5]-8-methyl-undecen-3-en-5-oxa-2-ol, MS) (MW: 168,22) was dissolved in methanol and subsequently diluted in PBS phosphate buffer, obtaining a final concentration of 1 mg/ml. The compound was stored at −80° C. until the use. Methanol ($CH_3OH$) concentration in the final solution was 2.5%. As a control cells were treated only with same $CH_3OH$ concentration and no toxicity effects were detected.

Materials and Methods
Cell Lines and Culture Conditions

The study has been carried out using representative tumor cell lines with different histological origin: MCF-7 breast carcinoma (human), M14 (human) and B16 (murine) melanomas, H125 (human) pulmonary carcinoma, HT-29 (human) colon carcinoma, HL-60 (human) promyelocytic leukemia.

All cell lines have been cultured in RPMI-1640 (Hyclone Europe, Cramlington, UK) medium supplemented with 10% of heat inactivated (56° C., 30 minutes) bovine fetal serum (Hyclone Laboratories, Logan, Utah), 2 mM L-glutamine and antibiotics (Life Technologies Ltd., Paisley, Scotland) (complete medium, CM). Cells have been stored at 37° C. in humidified atmosphere with 5% $CO_2$.

Cell suspensions (HL-60) have been harvested and counted. Plastic adherent cells, in semi-confluence condition, have been detached by a short exposure at 0.025% trypsin with 0.01% EDTA and counted.

Cell Proliferation and Viability Determination

All used tumor cells have been harvested, suspended in CM and seeded in 24-well plates at $10^5$ cell concentration in a final volume of 2 ml/well. For adherent cells a pre-incubation for 18 hours has been carried out in order to promote the adhesion to plastic. Subsequently cells have been treated with serial concentrations of methyl-spirane (MS) from 0.0125 μg/ml to1 100 μg/ml (0.0125, 0.125, 1.25, 12.5, 25, 50, 100 μg/ml) at culture times varying from 24 to 120 hours. Every treatment has been carried out in triplicate. The cell proliferation, viability and death have been determined by means of cell counts in trypan blue (dye exclusion test) using a hemocytometer.

Cell Apoptosis, Necrosis and Cycle by Means of Flow Cytometry Analysis

For apoptosis and cellular cycle analysis, control or various concentration MS treated cells have been removed from the culture by means of trypsinization, re-suspended in PBS, washed two times with cold PBS and fixed with 50% of acetone and methanol (1:4) in PBS at 4° C. Fixed cells then were washed in PBS and stained with propidium iodide 50 μg/ml (PI) in the presence of RNase A 100 KU/ml.

Samples have been analyzed using a FACScan cytometer and fluorescence propidium red signals have been registered on linear scale. Cell fluorescence has been analyzed using a FACScan flow cytometer (Becton Dickinson, USA) using a 488 nm emitting argon laser. Data have been analyzed electronically excluding detritus and cell aggregates. In the red fluorescence, that is proportional to the DNA cell content, the apoptotic cells are represented by hypodiploid peak (cells with DNA fractioned content), easy distinguishable from the healthy cell DNA diploid peak. The fraction of the apoptotic cells is calculated integrating the pre-G1 peak. This cell fraction is representative for those having a PI decreasing coloration, considered a marker of DNA fragmentation, phenomenon associated to cell death by apoptosis. The analysis of cell cycle distribution after 24, 48 and 72 hours of MS treatment has been carried out using ModFitLT software (Becton Dickinson Immunocytometry Systems).

For the necrosis evaluation, an aliquot of not fixed cells ($1\times10^6$) was incubated with 40 μg/ml PI for 1.5 hour at 37° C. The samples, directly in their coloring solution, have been then analyzed using FACScan flow. Cytometer. Apoptotic cells have been detected by FSC/PI dot plot as $PI^{dim}$ peak, meanwhile $P^-$ and $PI^{bright}$ represent viable and necrotic cells, respectively.

Telomerasic Activity

Telomerasic activity was evaluated using TeloTAGGG Telomerase PCR ELISA kit, photometric enzymatic immunoassay from Roche (Mannheim, Germany). At time of the test, frozen pellet was lysed directly in the tests-tube using 80 μl of cold extraction buffer. Telomerase amplification was carried out by PCR (30 cycles, 94° C. 30 sec; 52° C. 30 sec; 72° C. 45 sec). Telomerasic activity was determined on the cell extracts according to the protocol recommended by the supplier. Sample absorbance (OD, optical density) was measured at 450 nm in a multi-well plate reader (SpectraCount, Pakard, Meriden, Conn., USA). In order to evaluate telomerasic activity, MCF-7, H-125 and M14 tumor cells were treated for 48 hours with serial doses of methyl-spirane (from 1.25 μg/ml to 50 μg/ml) as above described. Subsequently, the cells have been detached from culture plates by trypsinization, centrifuged, pelletized, and stored at −80° C. until the use.

Results
Cell Proliferation

Cell proliferation results show that cell lines treated with spiranes at different concentrations (0.0125, 0.125, 1.25, 12.5, 25, 50, 100 μg/ml), for culture times varying from 24 to 120 hours, the compounds always induce in all treated lines a remarkable inhibition of cell proliferation, depending on culture time and concentration.

In particular, results for cellular proliferation and viability of the cells treated with methyl-spirane are reported in FIGS. 1-6, for MCF-7 breast carcinoma, H125 pulmonary carcinoma, HT-29 colon carcinoma, M14 human melanoma, B16 murine melanoma, HL-60 promyelocytic leukemia cell lines. In FIG. 11 the effects of methyl-spirane in comparison to spirane on proliferation of human melanoma M14 cell line are shown.

Cell Cycle

Figure 1:
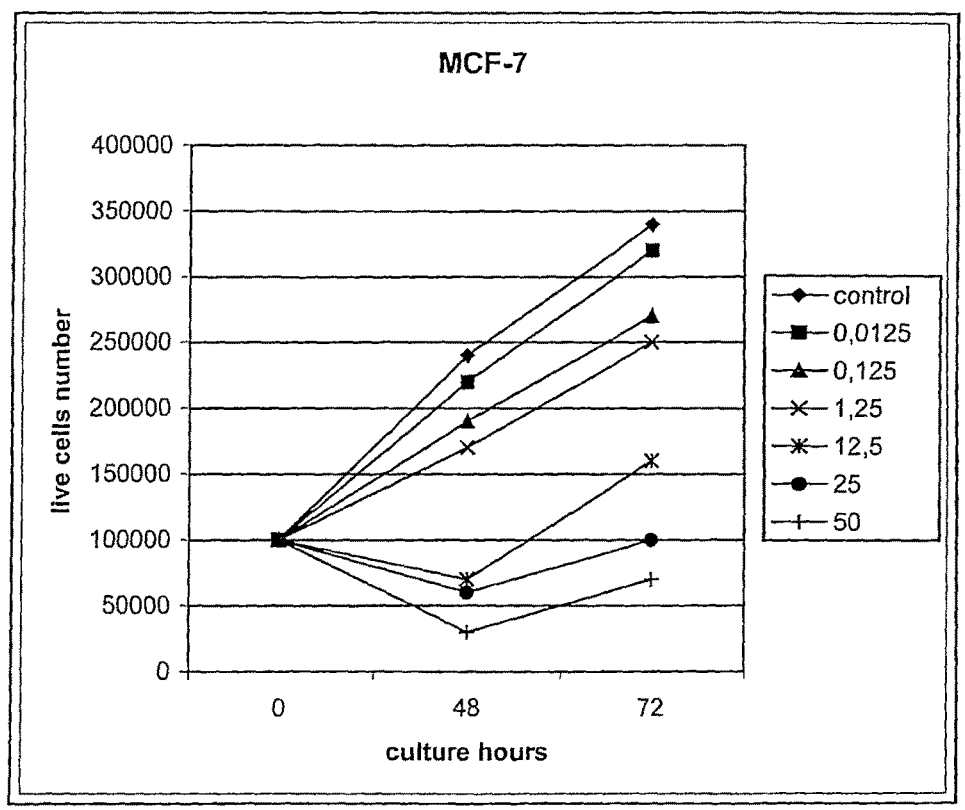
FIG. 1, shows results referring to assays of proliferation and viability of cells treated with control and methyl-spirane at different concentrations (0.0125, 0.125, 1.25, 12.5, 25, 50 μg/ml), respectively, carried out on breast carcinoma MCF-7 cell line.
Figure 2:
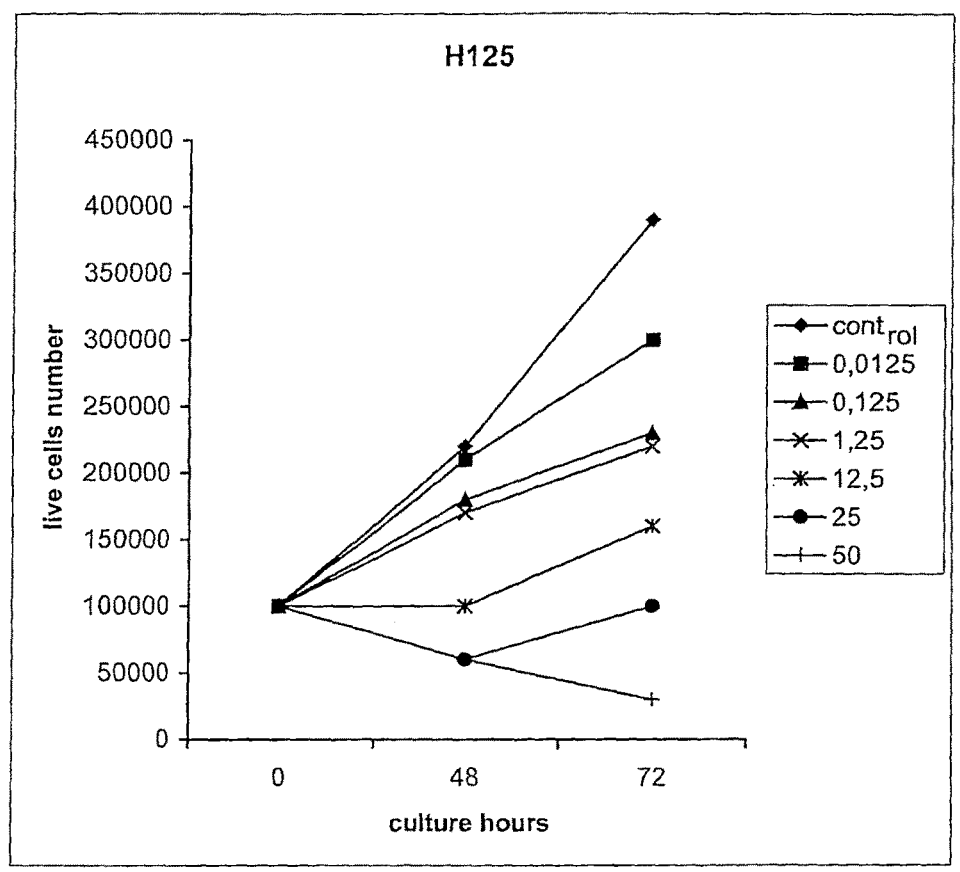
FIG. 2, shows results referring to assays of proliferation and viability of cells treated with control and methyl-spirane at different concentrations (0.0125, 0.125, 1.25, 12.5, 25, 50 μg/ml), respectively, carried out on pulmonary carcinoma H125 cell line.
Figure 3:
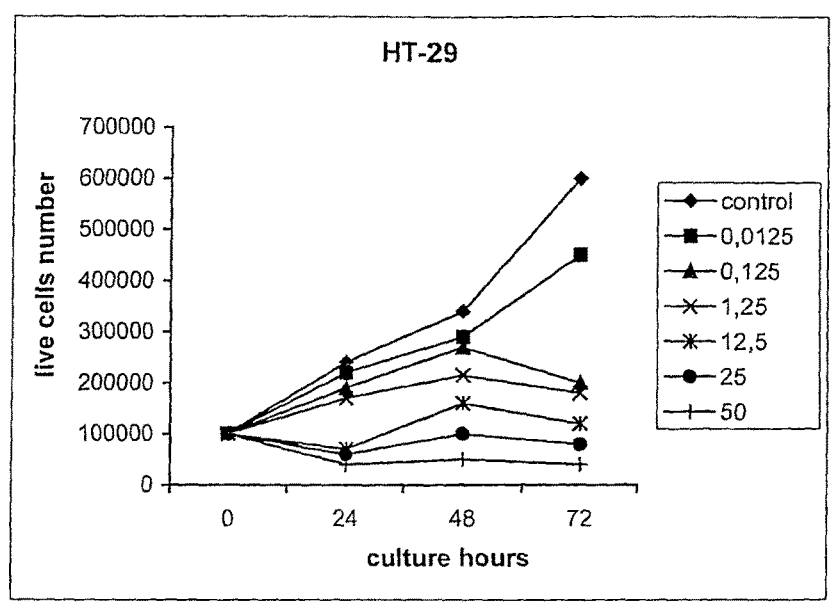
FIG. 3, shows results referring to assays of proliferation and viability of cells treated with control and methyl-spirane at different concentrations (0.0125, 0.125, 1.25, 12.5, 25, 50 μg/ml), respectively, carried out on colon carcinoma HT-29 cell line.
Figure 4:
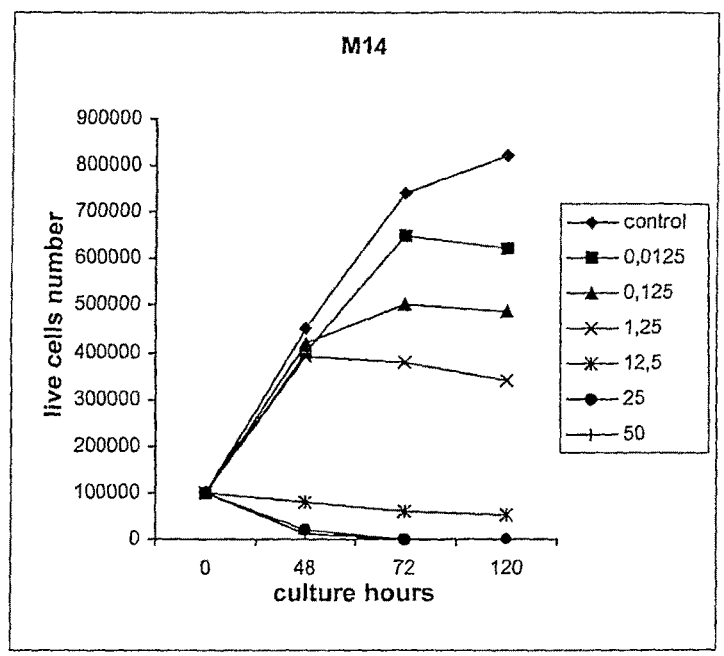
FIG. 4, shows results referring to assays of proliferation and viability of cells treated with control and methyl-spirane at different concentrations (0.0125, 0.125, 1.25, 12.5, 25, 50 μg/ml), respectively, carried out on human melanoma M14 cell line.
Figure 5:
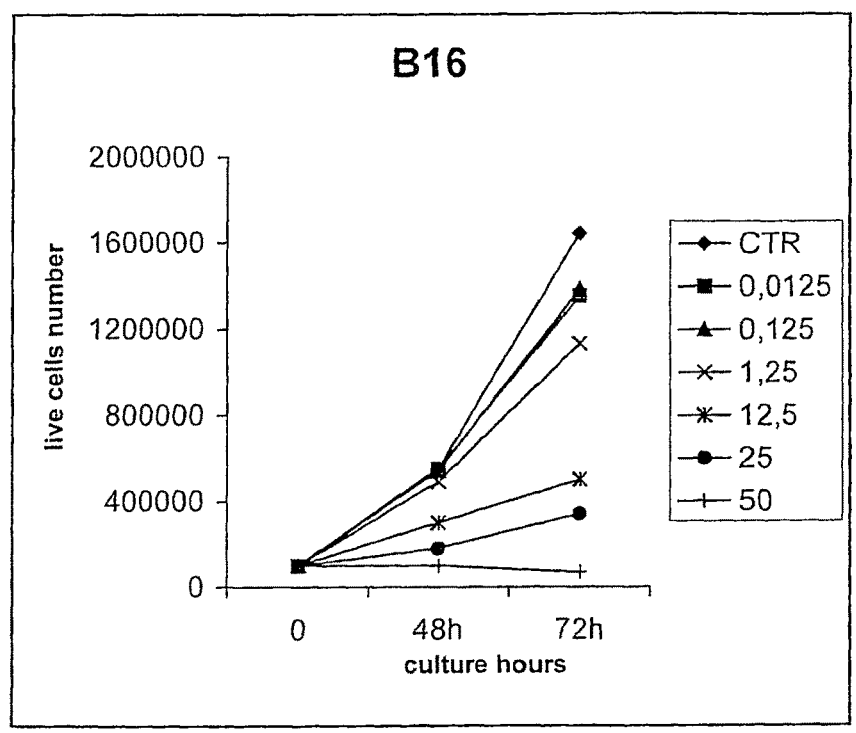
FIG. 5, shows results referring to assays of proliferation and viability of cells treated with control and methyl-spirane at different concentrations (0.0125, 0.125, 1.25, 12.5, 25, 50 μg/ml), respectively, carried out on murine melanoma B16 cell line.
Figure 6:
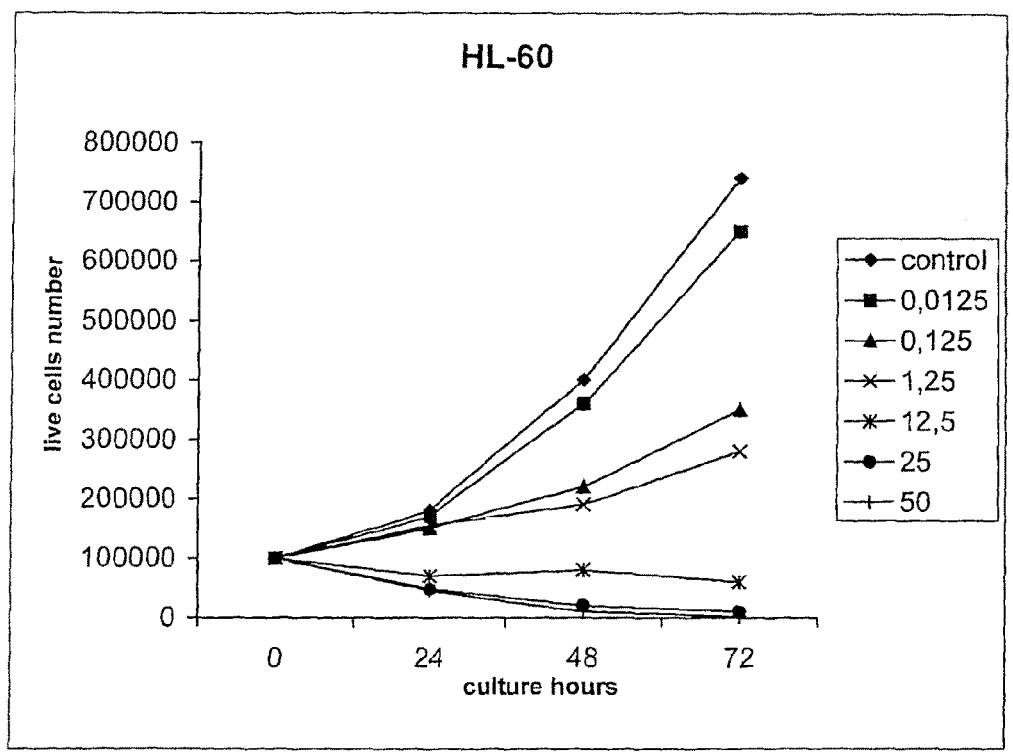
FIG. 6, shows results referring to assays of proliferation and viability of cells treated with control and methyl-spirane at different concentrations (0.0125, 0.125, 1.25, 12.5, 25, 50 μg/ml), respectively, carried out on promyelocytic leukemia HL-60 cell line.
Figure 7:
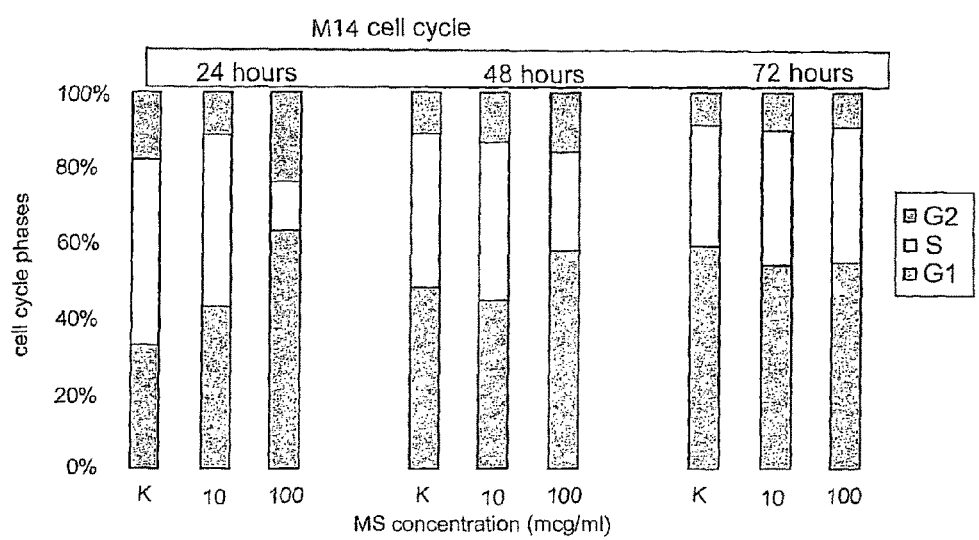
FIG. 7 shows the effect of the methyl spirane (MS) at various concentrations (10, 100 μg/ml) on cellular cycle of malignant melanoma M14 cell line wherein, starting from a 10 μg/ml dose an increment of G1 step is already detected after 24 hours treatment.

The effects of spiranes on cell cycle of the analyzed tumor cells show a response uniformity for the different analyzed cell lines. Generally after 24 hours of incubation in the presence of compounds the cell cycle is stopped, depending on the used concentration, at level of the passage from G1 to S step. As an example, the effect of methyl-spirane on M14 malignant melanoma cells wherein it is pointed out, starting from 10 µg/ml dose, an increment of the G1 step after 24 hours of treatment (FIG. 7).

Apoptosis and Necrosis

Figure 8:
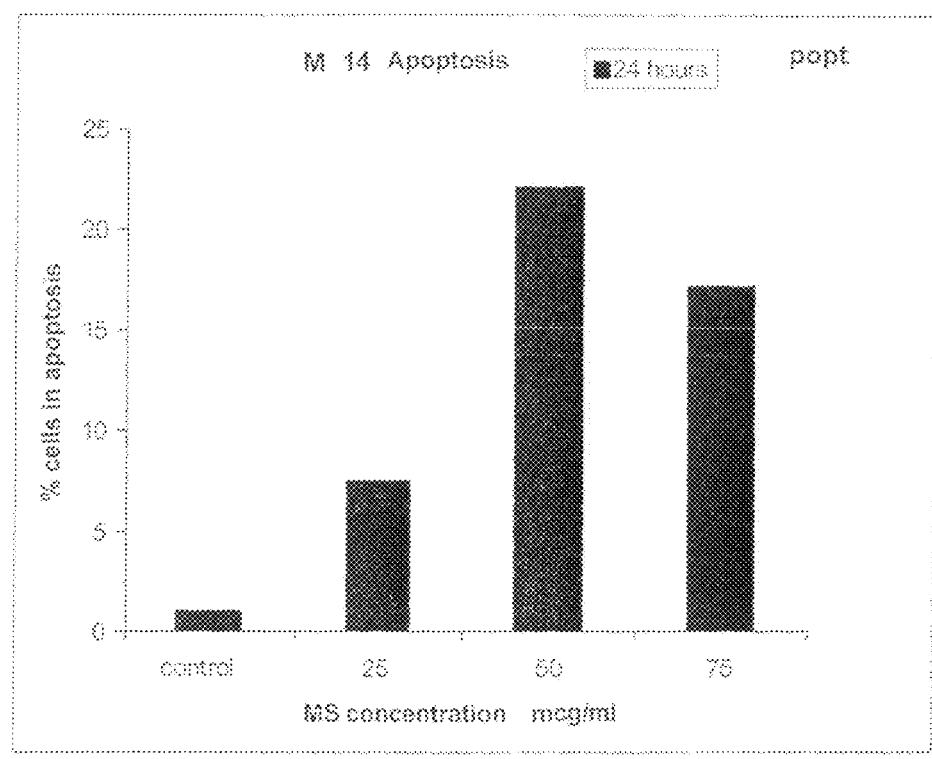
FIG. 8 shows the effect of methyl spirane (MS) on apoptosis induction at various concentrations (25, 50, 75 μg/ml) in malignant melanoma M14 cell line, wherein, starting from a 10 μg/ml dose an increment of G1 step is already detected after 24 hours treatment.
Figure 9:
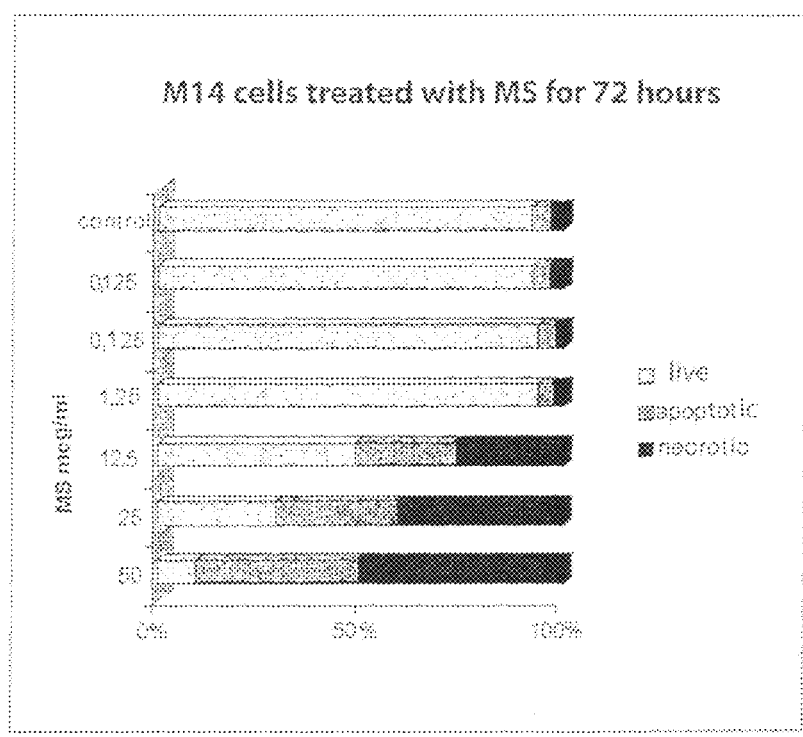
FIG. 9 shows the effect of methyl spirane (MS) on apoptosis induction and necrosis at various concentrations (25, 50, 75 μg/ml) in malignant melanoma M14 cell line, wherein, at concentrations higher than 1.25 μg/ml an apoptosis increment, concentration dependent, after 72 hours treatment is detected.

Results relating to apoptosis induction show that in cell lines treated with spiranes (0.0125, 0.125, 1.25, 12.5, 25, 50, 100 µg/ml), for variable culture times from 24 to 120 hours, are not detectable at low concentrations (0.0125 µg/ml-1.25 µg/ml) substantial changes in comparison to control, for all examined incubation times. At concentrations higher than 1.25 g/ml a variable apoptosis induction from 25 to 40% is observed. In the tumor cell lines examined at low concentrations (up to 1.25 µg/ml) no remarkable necrosis induction is observed, while from 12.5 µg/ml on a concentration-dependent increase up to 50% is observed. As an example, the effect of methyl-spirane (MS) on M14 cell line (melanoma) is reported, wherein apoptosis is already observed after 24 hours at MS concentration of 25 µg/ml (FIG. 8). Again with reference to M14 cell line in FIG. 9 results relating to the induction of apoptosis and necrosis after 72 hours of treatment are reported, wherein it is observed, at concentrations higher than 1.25 µg/ml, a concentration-dependent increase of apoptosis (30-50%).

Telomerase

Figure 10A:
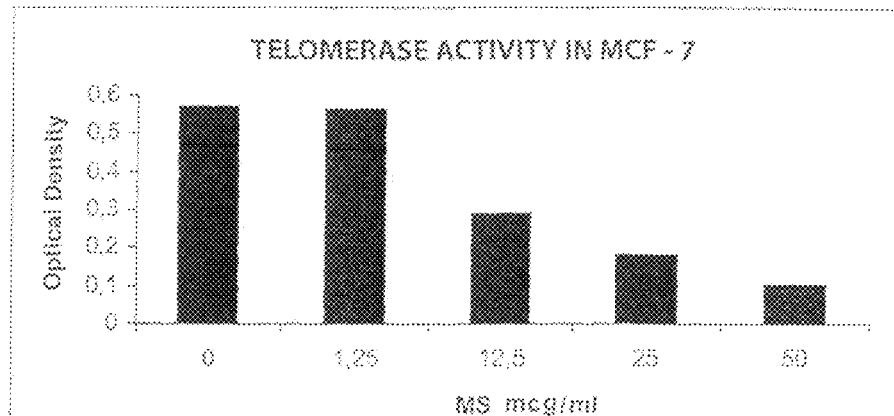
FIG. 10 shows the effect of methyl-spirane on telomerasic activity at various concentrations (1.25, 12.5, 25, 50 μg/ml) of MCF-7 (panel A), H-125 (panel B) and M14 (panel C) cell lines after 48 hours treatment.
Figure 10B:
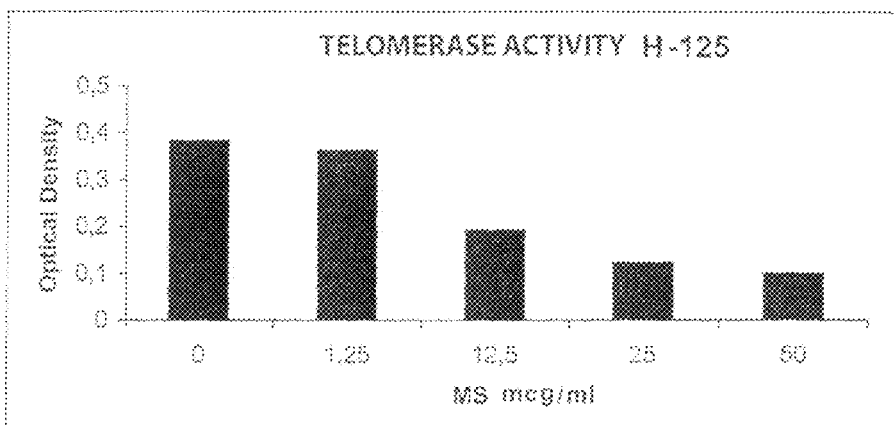
Figure 10C:
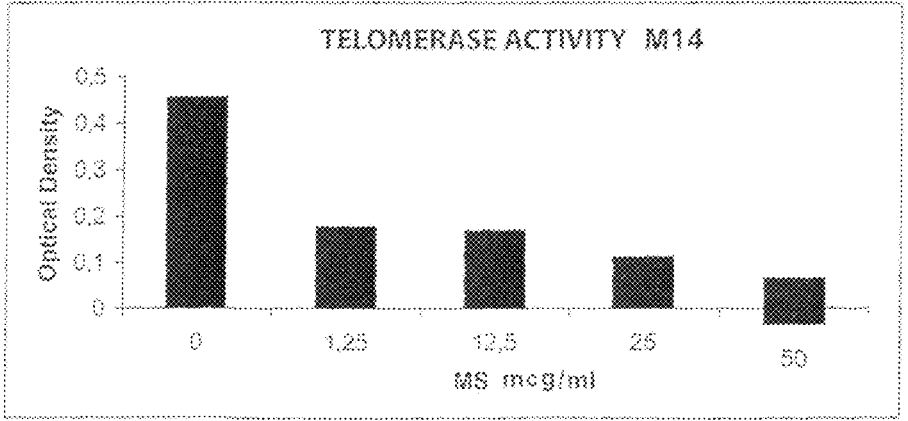

As to telomerase, the cells have been exposed in vitro at 1.25, 12.5, 25, 50 µg/ml of methyl-spirane and evaluated for telomerasic activity (TLMA) using ELISA assay, 48 hours after the treatment. Generally in all the examined cell lines a concentration-dependent reduction of the telomerasic activity is observed. Particularly, in the FIG. 10, panels A-C, the effects at various concentrations (1.25, 12.5, 25, 50) of methyl-spirane on MCF-7, H-125 and M14 cell, lines after 48 hours of treatment are shown.

Results of ELISA assay indicate that methyl-spirane at dose of 12.5 µg/ml results in a telomerase inhibition of 43%, 50% and 61% in comparison to control. At dose of 25 µg/ml, again in comparison to the control, the telomerase inhibition is 64%, 68% and 75%, respectively. At a dose of 50 µg/ml the inhibition is 80% and 75%, respectively. At concentration of the 1.25 µg/ml the enzymatic activity is very scarcely influenced in MCF-7 and H-125 cell lines.

These results clearly show that spiranes are suitable to display anti-tumor activity against tumor cells of various nature and histotype. Such activity in such cells is displayed through:

dose and time dependent inhibition of the growth,
dose and time dependent inhibition of the apoptosis,
dose and time dependent induction of cell cycle variation,
induction of a cell cycle stop at G1 step level.

EXAMPLE 3

Analysis for Spirane Toxicity on not Tumor Healthy Human Cells at Various Concentrations Lymphocytes (PBML) from 4 peripheral blood samples of healthy donors, separated by centrifugation on Fycoll gradient, have been treated with methyl-spirane at various concentrations: 12.5, 25, 50, 100 µg/ml. After 24 and 48 hours of culture, treated lymphocytes have been analyzed using supravital propidium iodide method (PI).

IN short this system is based on the use of propidium iodide, a fluorescent marker for the cellular DNA that normally penetrates only into the fixed or permeable made cells. PI supravital method is based on the principle that supravital exposure to propidium (high concentration of propidium for some hours at 37° C.) of not previously permeable made cells identifies in the population apoptotic cells clearly distinguishing them from necrotic or viable ones. Cells labeled with 40 µg/ml of propidium iodide directly in culture plates, are incubated at 37° for 1 hour and 30 minutes and analyzed using the flow cytometer.

Results point out that in all the samples treated with spiranes there is a concentration- and time-dependent increase of the necrotic cells, starting from 12.5 mcg/ml with simultaneous decrease of viable cell percentage. Obtained results evidence that at low concentrations the compound (for example, 1.25 µg/ml) displays inhibiting effects on the tumour cell growth in vitro (see MCF-7 cells) while on human lymphocytes (as model of not neoplastic healthy cells) no increase of necrosis with respect to the control is observed. Table 1 shows the values representative of a peripheral humans (PBL) lymphocyte sample from healthy donors treated for 48 hours with increasing concentrations of methyl-spirane

TABLE 1

| PBL treatment with methyl-spirane | % viable | % apoptotic | % necrotic |
| --- | --- | --- | --- |
| Control | 78.4 | 5.2 | 16.3 |
| 3.15 µg/ml | 81.5 | 2.5 | 16 |
| 6.25 µg/ml | 78 | 6.4 | 15.6 |
| 12.5 µg/ml | 29.7 | 30.1 | 40.0 |
| 25 µg/ml | 10.0 | 33.1 | 56.6 |
| 50 µg/ml | 8.2 | 21.7 | 70.0 |
| 100 µg/ml | 1.0 | 15.0 | 84.0 |

Presumably at low doses, although therapeutic and antiproliferative effect is maintained, toxic effects on healthy cells will not occur.

BIBLIOGRAPHY

Smith et al. the *Bioorganic & Medicinal Chemistry Letters* 2002, 12, 2039-2042.
Perron, F.; Albizati, K. *Chemical Reviews*, 1989, 86, 1617-1661.
Young et al. *Synthesis*, 2000, 13, 1956-1978.
Gallagher et al. *Tetrahedron Letters*, 2002, 43, 531-535.
Paterson et al. *Organic Letters*, 2002, 4, 391-394.
Brimble et al. *Tetrahedron*, 1999, 55, 7661-7706.
Malatesta et al. *Encyclopaedia of chemistry*, 1997, 6, 52-25, ISEDI.
Deslongchamps, P. *Stereoelettronic effects in organic chemistry*, 1983, Pergamon, Oxford.
Pouchert et al. *The Aldrich Library of $^{13}C$ and $^{1}H$-NMR Spectra*, 1993, 1, 407.
Pettit, G. *Journal of Natural Products*, 1996, 59, 812-821.
Uckun et al. *Bioorganic & Medicinal Chemistry Letters*, 2000, 10, 541-545.
Biard et al. *Journal of Natural Products*, 1994, 57, 1336-1345.
Watters et al. *Biochemical Pharmacology*, 1998, 55, 1691-98.
Amouroux R. *Heterocycles*, 1984, 22, 1489-92.
Georgiadis at al. *J. Org. Chem.* 1986, 51, 2725-2727.

Uckun et al. *Current Pharmaceutical Design*, 2001, 7, 1291-96.
Uckun F. *Current Pharmaceutical Design*, 2001, 7, 1627-39.
Watters et al. *Biochemical Pharmacology*, 1999, 58, 383-88.
Skoog West Holler. *Analitical Chemistry*, 1992, 387-90.
March, *Advanced Organic Chemistry*, 1992, 4 ed., Wiley Interscience.
Baker, J. Org. Chem. 1982, 47, 1292-1298.
Carey Sundberg, *Advanced Organic Chemistry*, 4 ed, 2002, part B, KA/PP.
Goodmann Gilmann, *Le Basi Farmacologiche della Terapia*, 9 ed, McGraw Hill, 1997.
Voet, Voet, Pratt, *Fondamenti di Biochinica*, 1 ed, Zanichelli Editore, 2001.
1999 Silverstein, Webster *Identificazione spettroscopica di cornposti organici,* 1 edz, Ambrosiana.

The invention claimed is:

1. Dioxaspiroketal derivative of formula (I):

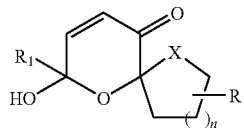

(I)

wherein R is $CH_3$, n is 2, X is O, $R_1$ is H,
or physiologically acceptable salts thereof.

* * * * *